United States Patent [19]

Pollock

[11] Patent Number: 4,966,599
[45] Date of Patent: Oct. 30, 1990

[54] ANATOMICAL PRECONTOURED PLATING, INSTRUMENTS AND METHODS

[76] Inventor: Richard A. Pollock, 5260 Riverview Rd., NW, Atlanta, Ga. 30327

[21] Appl. No.: 518,221

[22] Filed: May 3, 1990

Related U.S. Application Data

[63] Continuation of Ser. No. 274,699, Nov. 15, 1988, abandoned, which is a continuation of Ser. No. 35,658, Apr. 7, 1987, abandoned.

[51] Int. Cl.⁵ ............................................. A61B 17/58
[52] U.S. Cl. ..................................... 606/69; 206/457
[58] Field of Search ................ 206/457, 458; 434/267, 434/270, 274; 128/92 R, 92 Y, 92 YP, 92 YL, 92 YJ, 92 V, 92 VS; 606/69

[56] References Cited

U.S. PATENT DOCUMENTS

| | | | |
|---|---|---|---|
| 6,729 | 11/1875 | Cummings | 411/403 |
| 975,285 | 11/1910 | Robertson | 411/403 |
| 1,301,398 | 4/1919 | Day | 411/403 |
| 2,839,815 | 6/1958 | Reeves | 27/21 |
| 3,178,728 | 4/1965 | Christensen | 3/1 |
| 3,488,779 | 1/1970 | Christensen | 3/1 |
| 3,579,643 | 5/1971 | Morgan | 3/1 |
| 3,623,249 | 11/1971 | Brooks | 206/457 X |
| 3,683,422 | 8/1972 | Stemmer et al. | 3/1 |
| 3,720,959 | 3/1973 | Hahn | 3/1 |
| 3,742,943 | 7/1973 | Malmin | 128/76 |
| 3,835,848 | 9/1974 | Berner | 128/76 |
| 3,955,567 | 5/1976 | Richmond et al. | 128/92 |
| 4,040,129 | 8/1977 | Steinmann et al. | 420/422 X |
| 4,356,572 | 11/1982 | Guillemin et al. | 128/924 R X |
| 4,365,356 | 12/1982 | Broemer et al. | 128/924 Q X |
| 4,371,077 | 2/1983 | Solitt et al. | 206/458 X |
| 4,503,848 | 3/1985 | Caspar et al. | 128/92 |
| 4,512,038 | 4/1985 | Alexander et al. | 3/1.9 |
| 4,524,765 | 6/1985 | Zbikowski | 128/92 |
| 4,619,655 | 10/1986 | Hanker et al. | 128/90 X |
| 4,655,203 | 4/1987 | Tormala et al. | 128/92 YP |

FOREIGN PATENT DOCUMENTS 2472373 7/1981 France ............................ 128/92 YP

OTHER PUBLICATIONS

Vitallium Surgical Appliances Spinal Fusion Plates, 1948.

(List continued on next page.)

Primary Examiner—Robert A. Hafer
Assistant Examiner—Kevin G. Rooney
Attorney, Agent, or Firm—Kilpatrick & Cody

[57] ABSTRACT

Precontoured plating, screws, instruments and methods for osteosynthesis. Plates according to the present invention take advantage of the fact that human adult craniofacial structure and shape is highly similar among the population. The plates are thus preformed, pretempered, precontoured, and preconfigured during manufacture to fit a large proportion of the human adult population. The plates consequently require less time during surgery to twist and bend to conform to the skeletal structure and their crystalline and other structural characteristics need not be adversely affected by extensive bending, twisting and shaping in the operating room. The plates may be packaged and presented for use on forms which simulate portions of the skull so that their intended craniofacial location is easily recognized by members of the surgical team. Because bone thickness at particular craniofacial skeletal locations is highly consistent in the adult population, appropriate length screws may also be packaged with the plates with which they are to be used, as for instance, by insertion through the plates on the skeletal-shaped packaging form. The packaging also allows the plates to be pre-sterilized to save time which would otherwise be used for sterilizing the plates. Screws, screw transport units and starters and dispensers for the plates and screws are also disclosed.

21 Claims, 10 Drawing Sheets

OTHER PUBLICATIONS

Allgower, M., Cinderella of Surgery—Fractures?, 58 Surgical Clinics of North America 1071-93 (1978).

Allgower, M. et al., A New Plate For Internal Fixation—The Dynamic Compression Plate (DCP), 2 Injury 40 (1970).

Arons, M., Figure-of-Eight Wiring—Variations Cited (single page).

Bagby, G., The Effect of Compression on the Rate of Fracture Healing Using a Special Plate, 95 Am. J. Surg. 761-71 (1958).

Battersby, T., Plating of Mandibular Fractures, British J. Oral Surg. 194-201 (no date).

Becker, R., Stable Compression Plate Fixation of Mandibular Fractures, 12 British J. Oral Surg. 13-23 (1974).

Beckers, H., Treatment of Initially Infected Mandibular Fractures With Bone Plates, 37 J. Oral Surg. 310-13 (1979).

Billingsley, M. et al., Military Benefits From The Use Of Compressive Bone Plates In Mandibular Fractures: Case Report, 148 Military Medicine 162 (1983).

Bonnette, G., Experimental Fractures of the Mandible, pp. 568-71 (work and date not identified).

Bos, R. et al., Resorbable Poly(L-lactide). Plates and Screws for the Fixation of Zygomatic Fractures, 45 J. Oral Maxillofacial Surg. 751-53 (1987).

Bowerman, J. et al., A Universal Kit in Titanium for Immediate Replacement of the Resected Mandible, 6 British J. Oral Surg. 223-28 (1969).

Bradley, F. et al, A Depth Gauge for Assessing the Length of Screw Required in Mandibular Plating, 13 British J. Oral Surg. 100-01 (1975).

Brody, G., Small Holes, Small Bones, and Mandibular Stability, 2 Annals of Plastic Surgery 259 (1979).

Bruce, R. et al., Mandibular-Fracture Repair in Monkeys, 49 J. Dental Research 365 (1970).

Butow, unidentified title, British J. Oral and Maxillofacial Surg. 453-54 (no date).

Byars, L., Subperiosteal Mandibular Resection with Internal Bar Fixation (work unidentified). pp. 236-39 (1946).

Cawood, J., Small Plate Osteosynthesis of Mandibular Fractures, 23 British J. Oral and Maxillofacial Surg. 77-91 (1985).

Champy, M. et al., Mandibular Osteosynthesis by Miniature Screwed Plates Via a Buccal Approach, 6 J. Max.-Fac. Surg. 14-21 (1978).

Chandler, R., Limitations of Conventional Nailing, 8 Orthopedics 1354 (1985).

Cohen, J. et al., Mandibular Reconstruction, Open Reduction and Internal Fixation of Mandibular Fractures, 90 Otolaryngol Head Neck Surg 577-82 (1982).

Drommer, R., The Use of the Luhr Miniplate System in the Facial Skeleton, Maxillofacial Trauma: An International Perspective, pp. 255-61 (1983 Jacobs, ed.).

Eisendrath, D., Fractures, Surgery, Its Principles and Practice, pp. 415-26 (1909 Saunders).

Ewers, R., Experimental and Clinical Results of New Advances in the Treatment of Facial Trauma, Plastic and Reconstructive Surg. 25-31 (Jan. 1985).

Haynes, H., Treating Fractures by Skeletal Fixation of the Individual Bone, 32 Southern M. J. 720 (1939).

Helsham, R., An Evaluation of Lower Border Wiring, Australian Dental Journal 435 (1968).

Hickman, D. et al., A Technical Aid in Transoral Wiring of Mandibular Fractures (pp. 90-92).

Hilger, P., The Dynamic Compression Plate for Mandibular Fixation, Plastic and Reconstructive Surgery of the Head and Neck, Volume 2, pp. 222-24 (1981 Bernstein, ed.).

Howmedica, Luhr Mini-Compression System for Surgery of the Midface Skeleton and Orthognatic Surgery (1985).

Howmedica, Luhr Mandibular Compression-Screw-System for Mandibular Fractures (1985).

Johnson, K., Indications, Instrumentation, and Experience with Locked Tibial Nails, 8 Orthopedics 1377 (1985).

Jones, R., Military Orthopedic Surgery, Surgery, Its Principles and Practice, pp. 624-75 (1909 Saunders).

Kahnberg, K., Bone Plate Fixation of Mandibular Fractures, 9 Int. J. Oral Surg. 267-73 (1980).

Kellman, R., Repair of Mandibular Fractures Via Compression Plating and More Traditional Techniques: A Comparison of Results, 94 Laryngoscope 1560 (1984).

Key, J. et al., Contact Splints (Eggers). vs. Standard Bone Plates in the Fixation of Experimental Fractures, 137 Annals of Surgery 911 (1953).

Khanna, J., Bone Plates in the Management of Mandibular Fractures, 56 J. Indian Dent. Asso. 95-102 (1984).

Kingsley, N., A Treatise On Oral Deformities (1880) (Title Page).

Klotch, D. et al., Plate Fixation For Open Mandibular Fractures, 95 Laryngoscope 1374 (1985).

Koberg, W. et al., Treatment of Fractures of the Articular Process by Functional Stable Osteosynthesis Using Miniaturized Dynamic Compression Plates, 7 Int. J. Oral Surg. 256-62 (1978).

Kruger, E. et al., Results of Bone Grafting After Rigid Fixation, 42 J. Oral Maxillofacial Surg. 491-96 (1984).

Levine, P., Mandibular Reconstruction: The Use of Open Reduction with Compression Plates, 90 Otolaryngol Head Neck Surg. 585-88 (1982).

Lopez, E., Use of a Dynamic Mini-Compression Plate for the Internal Fixation of Mandibular Fractures, Annals of Plastic Surgery 497-500 (1981).

Lorenz, Walter Surgical Instruments, Inc., Original Steinhauser (no date).

Lorenz, Walter Surgical Instruments, Inc., Wurzburg Titanium Miniplate System for Facial and Cranial Osteosynthesis (1986).

Lorenz, Walter Surgical Instruments, Inc., Maxillo-Facial Osteosynthesis using Small Plates according to Professor Champy (1985).

Medicon Instrumente, excerpts from catalog, pages for Steinhauser bone plates and instruments, 14 pp. (no date).

Michelet, A. et al, Osteosynthesis With Screwed Plates in Maxillofacial Surgery, 58 Int'l Surgery 249-253 (1973).

Michelet, F. et al., Osteosynthesis with Miniaturized Screwed Plates in Maxillo-Facial Surgery, 1 J. Max-Fac. Surg. 79-84 (1973).

Mooney, J. et al., Use of Wire Sutures For Fracture Fixation, 34 Oral Surg. 21-25 (1972).

Neal, G., Interosseous Wiring in the Treatment of (List continued on next page.)

OTHER PUBLICATIONS

Maxillofacial Trauma, 62 Ear Nose Throat J. 379-82 (1983).
Niederdellmann, H. et al., Photoelastic Behavior of Osteosynthesis Plates With Different Arrangement of Screw Holes for Mandibular Fractures, 4 Int. J. Oral Surg. 27-31 (1975).
Niederdellmann, H. et al., Internal Fixation of Fractures, 7 Int. J. Oral Surg. 252-55 (1978).
Niederdellmann, H. et al., Lag-Screw Osteosynthesis: A New Procedure for Treating Fractures of the Mandibular Angle, 39 J. Oral Surg. 938 (1981).
Panuska, H., Metallic Fixation of the Mandible by Open Reduction, 23 O.S., O.M. & O.P. 1148 (1967).
Paulus, G., Miniplattenosteosynthesen bei Traumatologischen sowie Korrektiven Operationen im Kiefer- und Gesichtbereich, 93 Schweiz. Mschr. Zahnheilk 705 (1983).
Petzel, J., Stability of the Mandibular Condylar Process After Functionally Stable Traction-Screw-Osteosynthesis (TSO) with a Self-Tapping Screw-Pin, 10 J. Max.-Fac. Surg 149-54 (1982).
Roed-Petersen, B., Absorbable Synthetic Suture Material for Internal Fixation of Fractures of the Mandible, 3 Int. J. Oral Surg. 133-36 (1974).
Schilli, W., Compression Osteosynthesis, 35 J. Oral Surg. 802 (1977).
Schilli, W. et al., Bone Fixation with Screws and Plates in the Maxillo-Facial Region, 10 Int. J. Oral Surg. 329-32 (1981).
Schmoker, R., Bulletin of Swiss Association for the Study of Internal Fixation, The Eccentric Dynamic Compression Plate (1976).
Schmoker, R., Rigid Internal Fixation of Compound Fractures of the Mandible Using a Specially Designed Reconstruction Plate, Maxillofacial Trauma: An International Perspective, pp. 187-99 (1983 Jacobs, ed.).
Schmoker, R., et al, Application of Functionally Stable Fixation in Maxillofacial Surgery According to the ASIF Principles, Technical Notes, American Association of Oral and Maxillofacial Surgeons (no date).
Schmoker, R., Mandibular Reconstruction Using a Special Plate, 11 J. Max.-Fac. Surg. 99-106 (1983).
Shrewsbury, D. et al., Repair of Complicated Mandibular Defects, 108 Arch. Otolaryngol 162 (1982).
Souyris, F. et al., Treatment of Mandibular Fractures by Intraoral Placement of Bone Plates, 38 J. Oral Surg. 33 (1980).
Spiegel, P., How Not to Do Compression Techniques, Unidentified Work, pp. 61-64, (February, 1979).
Spiessl, B., A New Method of Anatomical Reconstruction of Extensive Defects of the Mandible with Autogenous Cancellous Bone, 8 J. Max.-Fac. Surg. 78-83 (1980).
Spiessl, B., Rigid Internal Fixation of Fractures of the Lower Jaw, 13 Reconstr. Surg. Traumat. 124-40 (1972).
Speissl, B., Early Treatment of Complicated Mandibular Fractures by Means of Rigid Internal Fixation According to AO Principles, Maxillofacial Trauma: An International Perspective, pp. 177-86 (1983 Jacobs, ed.).
Strelzow, V. et al., Dynamic Compression Plating in the Treatment of Mandibular Fractures, 108 Arch. Otolaryngol 583 (1982).
Strelzow, V. et al., An Internal Compression Plating Approach to the Management of Maxillo-Facial Fractures, Maxillofacial Trauma: An International Perspective, pp. 245-54 (1983 Jacobs, ed.).
Strelzow, V. et al., Osteosynthesis of Mandibular Fractures in the Angle Region, 109 Arch. Otolaryngol (1983).
Synthes Maxillofacial, 1986 Catalog: Original AO/-ASIF Instruments and Implants for Maxillofacial Bone Surgery.
Synthes Maxillofacial, 1986 Catalog: Original Swiss ITI Oral Implant System.
Synthes Maxillofacial, 1986 Catalog: KaVo Drill System.
Synthes Ltd. (USA), Bulletin 70, Internal Fixator For The Spine, 6 pages.
Synthes Ltd. (USA), 1986 Price List.
Synthes Ltd. (USA), 1985 Price List.
Synthes Maxillofacial, 1986 Price List.
Synthes Ltd. (USA), 1985 Catalog: Original ASIF (Association For The Study Of Internal Fixation) Instruments and Implants.
Szabo, G., Champy Plates in Mandibular Surgery, 13 Int. J. Oral Surg. 290-93 (1984).
Tu, H., Compression Osteosynthesis of Mandibular Fractures, 43 J. Oral Maxillofacial Surg. 585-89 (1985).
Van Dijk, L. et al., Treatment of Mandibular Fractures by Means of Stable Internal Wire Fixation, 6 Int. J. Oral Surg. 173-76 (1977).
One page of notes entitled "Mandible".
One page of notes entitled "Gruss 8-20-84".
Two Pages of Notes entitled "Klotch".

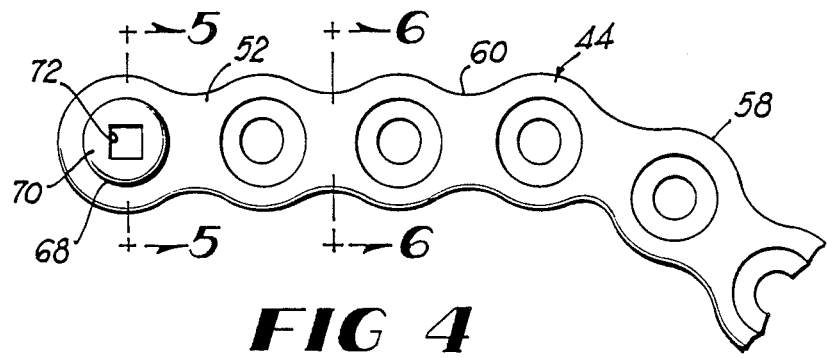
FIG 4
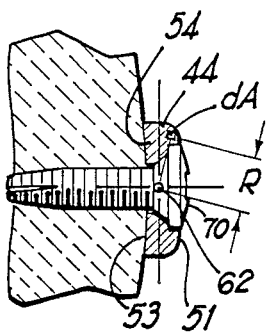 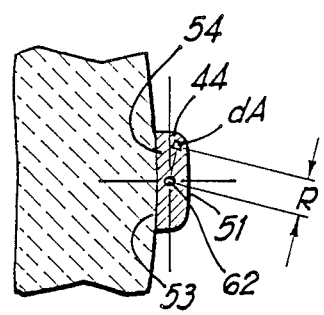
FIG 5   FIG 6
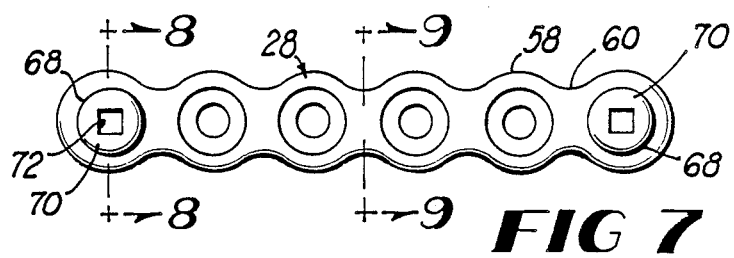
FIG 7
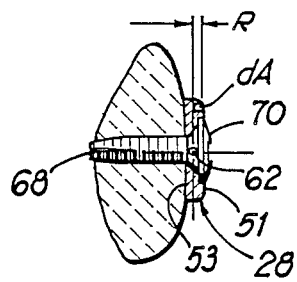 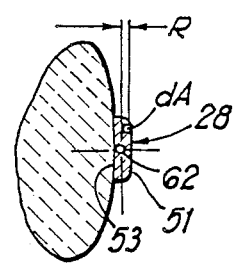
FIG 8   FIG 9

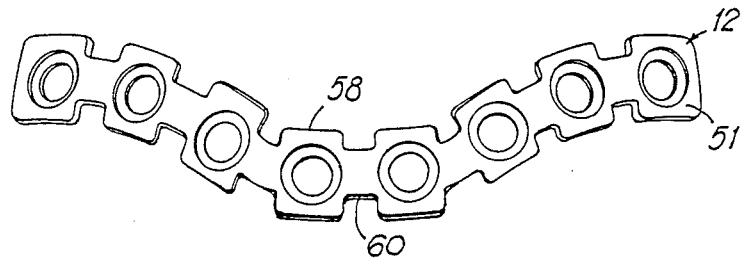
FIG. 11A
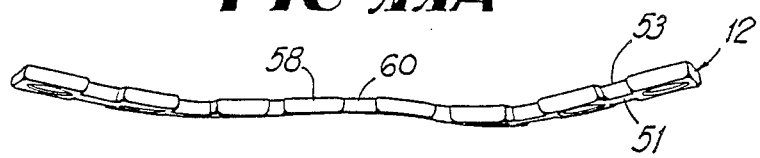
FIG. 11B
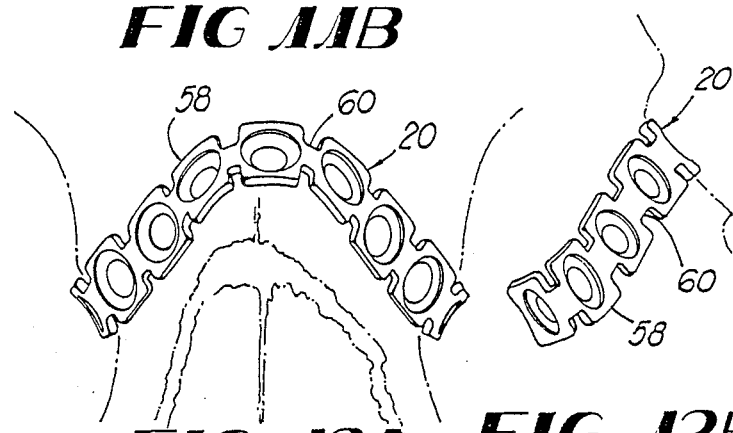
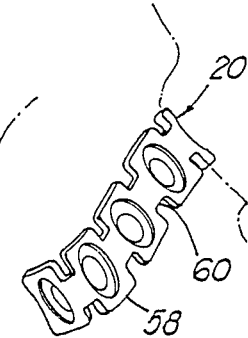
FIG. 12A    FIG. 12B
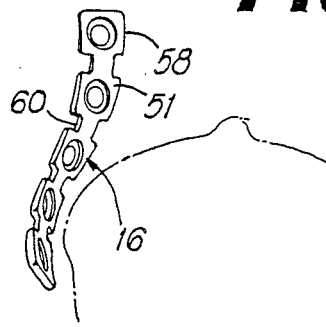
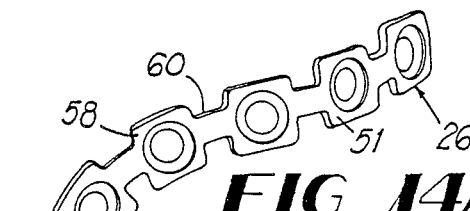
FIG. 14A
FIG. 13
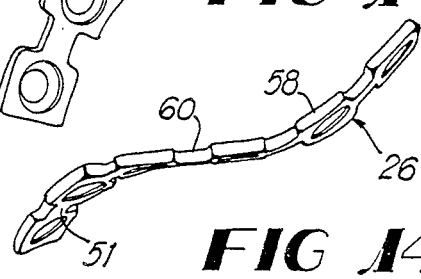
FIG. 14B

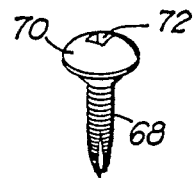
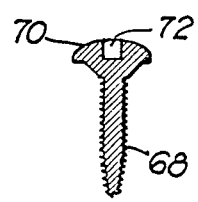
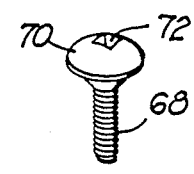
FIG 22   FIG 23   FIG 24
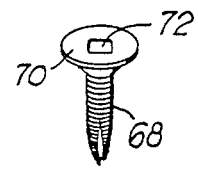
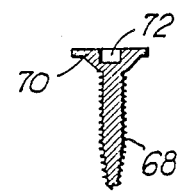
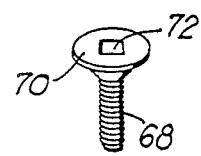
FIG 25   FIG 26   FIG 27
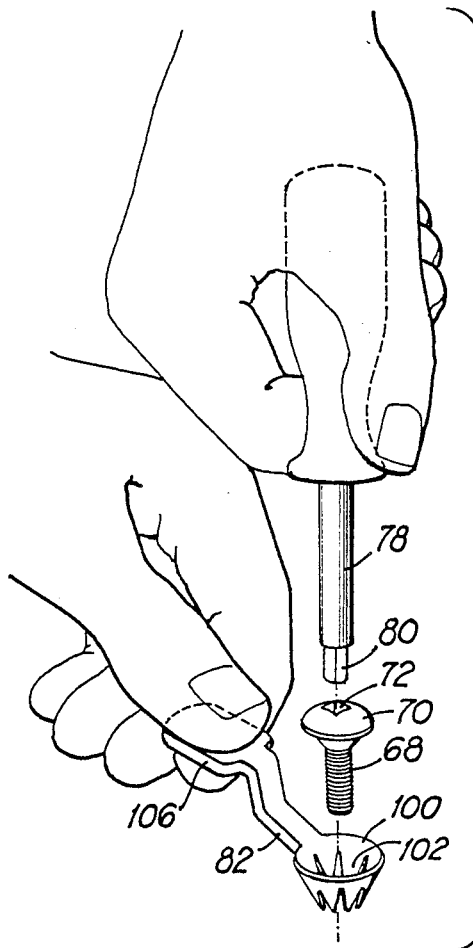
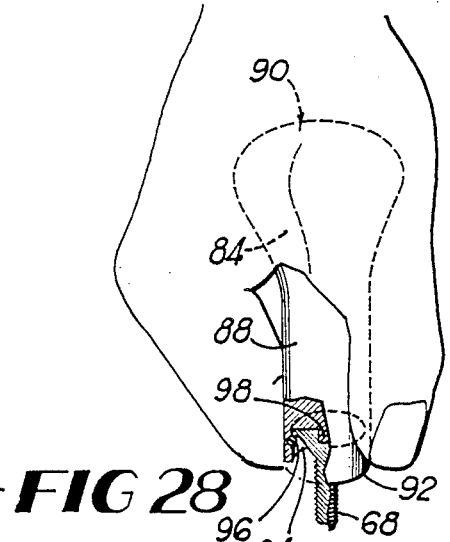
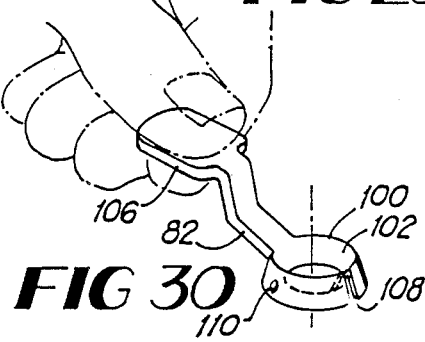
FIG 28   FIG 29   FIG 30

ANATOMICAL PRECONTOURED PLATING, INSTRUMENTS AND METHODS

This is a continuation of copending application for Anatomical Precontoured Plating, Instruments and Methods, Ser. No. 274,699, filed on Nov. 15, 1988, now abandoned, which is in turn a continuation of patent application for Anatomical Precontoured Plating, Instruments and Methods, Ser. No. 035,658, filed Apr. 7, 1987, now abandoned.

This invention relates to three-dimensionally shaped osteosynthesis plates for alignment and stabilization of fractured bones. Other aspects of the invention include fasteners and instruments for securing the plates to the skeleton and devices and methods for packaging, transporting and installing the plates and fasteners.

BACKGROUND OF THE INVENTION

Repair of dislocated bone involves two primary steps: realignment of the dislocated fragments or segments and stabilization of the bone. Dressings such as plaster or oil-soaked linen and wire have been used since antiquity for bone stabilization, but wire emerged as the prevalent appliance for bone stabilization in the nineteenth century.

Placement of wire loops through holes drilled in bone has long been an accepted technique, but more recent experience, during and after World War II, suggested that bone repaired with wire loops is not rigidly stable. The advent of mechanization and concomitant faster travel resulted in high velocity injuries more severe in nature than those previously encountered. Experience in treatment of such injuries has made it evident that bone fragments connected by wire loops are free to hinge along the fracture line. This bone fragment mobility interferes with healing and results in delayed recovery, skeletal deformity including midfacial shortening, and high rates of infection. Patients with complex injuries have often been crippled or disfigured for life, and many such injuries have been fatal.

Crude metal plates were introduced in Europe in approximately 1957 for the repair of orthopedic fractures. These plates, which were secured to bone with screws, advantageously prevented the bone fragment mobility that is often associated with wire-stabilized injuries. Subsequent generations of plates and fasteners, together with new instruments, allowed rigid stabilization of orthopedic and craniofacial fractures to become a reality. Complex, comminuted and severely dislocated fractures could then be effectively treated.

Typical of plates presently provided for cranial and facial osteosynthesis include those of the Wurzburg, Steinhauser and Champy systems sold in the United States by Walter Lorenz Surgical Instruments, Inc., Jacksonville, Florida, plates of Synthes, Inc., Basel, Switzerland and Paoli, Pennsylvania, and compression plates provided by Howmedica International, Inc., Kiel, Federal Republic of Germany. These plates present common, severe disadvantages, however.

Such plates typically comprise small, generally flat, elongated sections of metal. The sections contain round and perhaps elongated screw holes at various points along their lengths for fastening the sections to bone. The sections may be linear, curved, T-shaped, L-shaped or otherwise angled in their generally planar dimensions for positioning on various portions of the skeleton.

Because no surface of the human skeleton is flat, existing plates must be extensively twisted, formed and bent during surgery to conform to portions of the skeleton on which they are to be affixed. During a six to eight hour surgical procedure, as much as 30 to 45 minutes of time may be expended shaping and re-shaping metal plates. This additional time increases anesthesia requirements and operating room time and increases the potential of infection.

The inevitable over-bending and under-bending of plates during efforts to form the plates during surgery creates crimps and other surface imperfections in the plates and it alters their structural integrity due to metal fatigue. Surface imperfections can also irritate overlying tissue. Weakened structure due to excessive bending and twisting in the operating room is of paramount importance because it can lead to structural failure later; these plates frequently must remain in patients' faces for the rest of their lives and must undergo tremendous stresses, as for instance in the mandibular or ramus areas.

The heads of screws provided with present plates extend beyond the plane of the outer surfaces of the plates and create voids between bone and the periosteal lining. The contour of screw heads and often the plates are frequently transmitted through overlying soft tissue and thereby made visible on the patient's face; both screw heads and plates therefore frequently may be palpated beneath the skin's surface.

The planar nature of conventional plates increases this problem of transmission through the facial soft tissue. Rather than having edges which conform to and grip the bone, the edges of present plates frequently form a tangent with respect to the skeleton so that the patient may actually be able to push subcutaneous tissue between the plate edge and bone with his or her fingernail.

Known packaging techniques present additional difficulties. Plates and screws are presently provided on pegs or in slots together with installation tools in perforated metal boxes. They are arranged in various sizes, shapes and lengths and cannot be easily identified by name, so the surgeon finds it difficult to tell the nurse which plate will be used next. The plates and screws packaged in these metal boxes also require sterilization in an autoclave or other apparatus, so that addition valuable time prior to or during surgery is lost.

Conventional plates, screws and instruments are held in place by gravity in their metal boxes. If such a box is inverted while closed, the plates, screws and instruments become scrambled in the box. If the box is open while it is inverted or dropped, the plates, screws and instruments are scattered about the operational setting.

Screws must be delivered from the scrub nurse's station or table to the surgeon by means which allow them to be quickly and easily used. Present techniques include Phillips or cruciform head screwdrivers with clutches that grab the screwhead. The clutch sleeve is retracted once the screw is started into the bone. Such clutches are difficult to engage and disengage from screwheads, particularly after repeated use, because of rust in the clutch mechanism. The additional force required to disengage the clutch may jar delicate bone such as, for example, the bone of the inferior orbital rim. On the other hand, Phillips, slotted or cruciform screwdrivers without a clutch can disengage from the screwhead and interrupt insertion of the screw, alter the torque axis or alter screw penetration direction if the screw is self-tapping. Many existing screw designs also result in inadvertent disengagement or slippage of the screwdriver from the head. Existing slotted, cruciform or hexagonal-type screwheads all allow this disengagement.

SUMMARY OF THE INVENTION

The present invention provides plates, screws, instruments and methods which have been found to overcome these deficiencies. The invention takes advantage of the surprising fact that human adult craniofacial osseous structure and shape are highly similar among the population. Accordingly, plates can be preformed during manufacture to fit a large proportion of the human adult population. Consequently, less time is required during surgery to twist and bend the plates, and their structural characteristics need not be adversely affected by extensive bending, twisting and shaping. Furthermore, they can be made of harder and stiffer material and thus perform more effectively, since they do not need to be soft enough to allow the surgeon to bend and twist them easily in the operating room.

The plates may be packaged and presented for use on forms which simulate portions of the skull, so that their intended cranial or facial position is more easily recognized by members of the surgical team. Because bone thickness at particular craniofacial skeletal locations is highly consistent in the adult population, appropriate length screws may be packaged with the plates with which they are to be used, as for instance, by insertion through or adjacent to the plates on the skull-like packaging platform. Important surgical time is thus saved in selecting screws.

Screws for use with the present invention may have square-shaped recesses in order to prevent stripping and inadvertent disengagement from the screwdriver. Square recessed heads allow for greater longitudinal control of the screws as they are started and for application of greater selected torque without disengagement of the screwdriver or failure of the screwdriver seat in the screwhead.

A first screw transport unit for transporting a screw from its packaging to the surgical field and for starting the screw in the bone has a recessed clutch that is precisely sized to receive the head of the screw. The screw starter features a square protrusion that matches the square recess of the screwhead and that is designed to absorb the torque necessary to start the screw into the bone. The screw starter is then removed and final tightening of the screw is completed with the square tipped screwdriver. A second transport system is a breakaway hub in which the screw can be dispensed. The hub has a clutch which is designed to capture precisely the head of the screwdriver. The screw is transported by the hub to the surgical field and started into the bone. The hub may contain a fault which fails upon application of a predetermined torque level or pressure so that the hub breaks away and can be removed with a tab or other means for easy retrieval. A radiographic marker may also be included in the hub.

Supplemental screws may be dispensed from a round compartmentalized container with a rotatable cover. A single opening allows access to a compartment which may contain one or more sterile screws of designated length and diameter. The screws may be contained in sealed, presterilized packaging. Supplemental plates may be dispensed from similar dispensers.

It is thus an object of the present invention to provide bone stabilization plates that are shaped in three dimensions during manufacturing to require less bending and contouring during surgery in order to save time, minimize surface irregularities in the installed plates and reduce metal fatigue due to bending and twisting.

It is an additional object of the present invention to provide bone stabilization plates that are arced in cross-section with respect to their longitudinal axes in order better to grip bone and minimize space between plate and bone.

It is an additional object of the present invention to provide bone stabilization plates that transmit fewer and smaller surface irregularities through the soft tissues of the patient's face.

It is a further object of the present invention to provide bone stabilization plates and groups of such plates which may be packaged mounted on forms resembling the portion of the craniofacial skeleton to which they will be attached, in order to allow all members of the surgical team more easily to recognize and refer to various plates and their intended position in use.

It is a further object of the present invention to provide bone stabilization plate fasteners whose heads have square recesses in order to minimize inadvertent disengagement of the screws from screwdrivers and to absorb greater torque with less chance of screw head failure.

It is a further object of the present invention to provide bone stabilization plate fasteners which are packaged with the plates mounted on forms resembling the portion of the craniofacial skeleton to which they will be attached, in order to minimize time necessary for screw selection and to allow for ease of reference by members of the surgical team.

It is a further object of the present invention to provide screw starters and transporters which allow screws to be more easily transported to the surgical field and which minimize potential for screw loss or improper starting into the bone.

It is a further object of the present invention to provide screw and plate dispensers which allow presterilized screws and plates to be dispensed easily and quickly and which facilitate accounting for screws and plates utilized during the operation.

It is a further object of the present invention to provide instruments for more efficient and effective application, stabilization and contouring of bone stabilization plates.

Other objects, features and advantages of the present invention will become apparent with reference to the remainder of the disclosure, claims and drawings.

BRIEF DESCRIPTION OF THE DRAWINGS

FIG. 4 is a plan view of a portion of the mandibular angle plate shown in FIG. 3.

FIG. 5 is a cross-sectional view of the plate of FIG. 4 taken along section 5—5 of that plate.

FIG. 6 is a cross-sectional view of the plate of FIG. 4 taken along sections 6—6 of that plate.

FIG. 7 is a plan view of the zygomatic arch plate shown in FIG. 3.

FIG. 8 is a cross-sectional view of the plate of FIG. 7 taken along section 8—8 of that plate.

FIG. 9 is a cross-sectional view of the plate of FIG. 7 taken along section 9—9 of that plate.

FIG. 11A is a front elevational view of a glabellar plate according to the present invention.

FIG. 11B is a plan view of the plate of FIG. 11A.

FIG. 12A is a front elevational view of a medial canthal plate according to the present invention.

FIG. 12B is a right side elevational view of the plate of FIG. 12A.

FIG. 13 is a front elevational view of a nasofrontal plate according to the present invention.

FIG. 14A is a front elevational view of a lateral buttress plate according to the present invention.

FIG. 14B is a plan view of the plate of FIG. 14A.

FIG. 22 is a perspective view of a first type of fastener according to the present invention.

FIG. 23 is a cross-sectional view of the fastener of FIG. 22.

FIG. 24 is a perspective view of a second type of fastener according to present invention.

FIG. 25 is a perspective view of a third type of fastener according to the present invention.

FIG. 26 is a cross-sectional view of the fastener of FIG. 25.

FIG. 27 is a perspective view of a fourth type of fastener according to the present invention.

FIG. 28 shows a first type of screw starter and a screwdriver according to the present invention.

FIG. 29 shows a second type of screw starter according to the present invention.

FIG. 30 shows a third type of screw starter according to present invention.

DETAILED DESCRIPTION OF THE DRAWINGS

Figure 1:
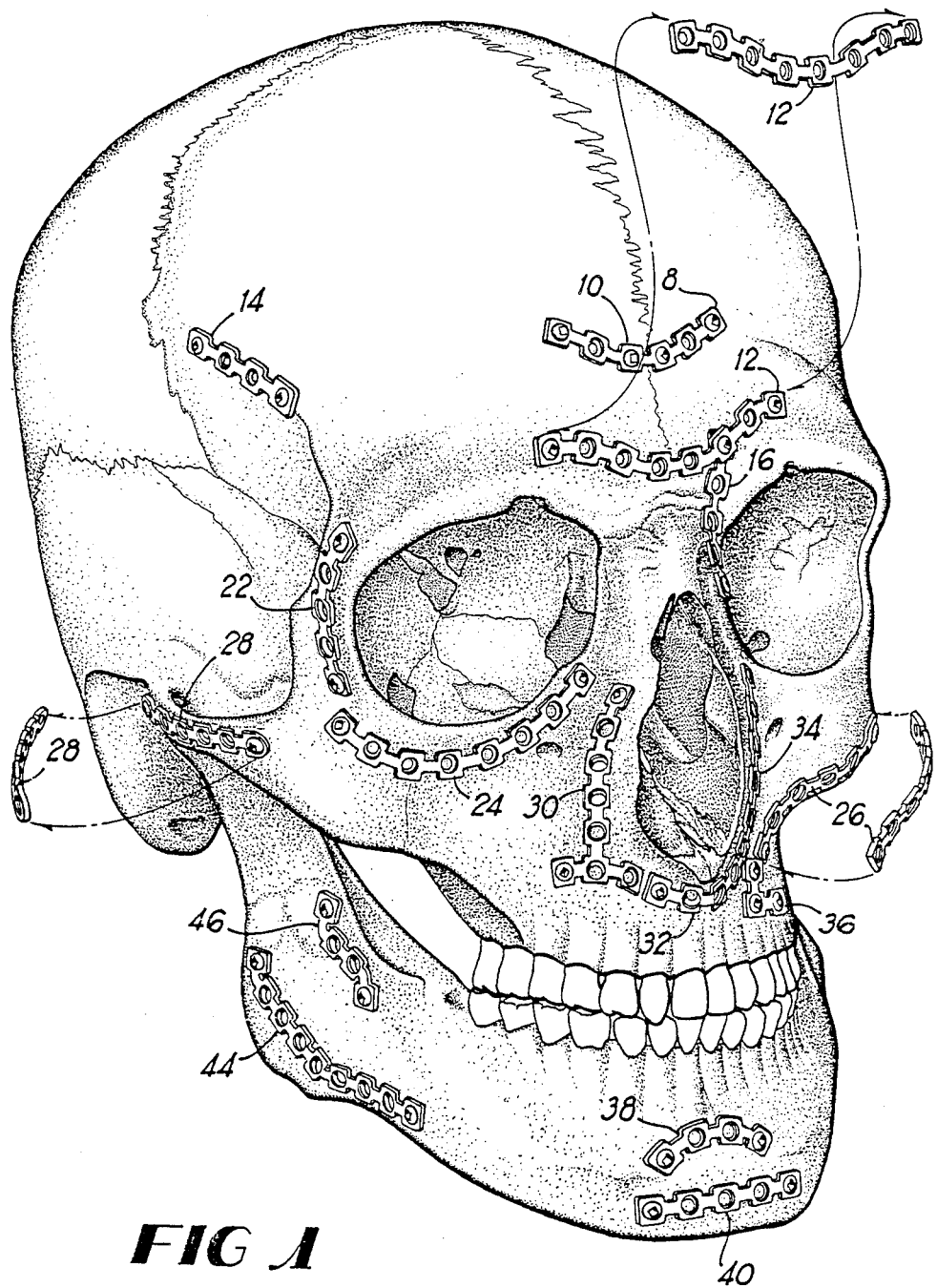
FIG. 1 is a perspective view of craniofacial structure showing installed bone stabilization plates according to the present invention.
Figure 2:
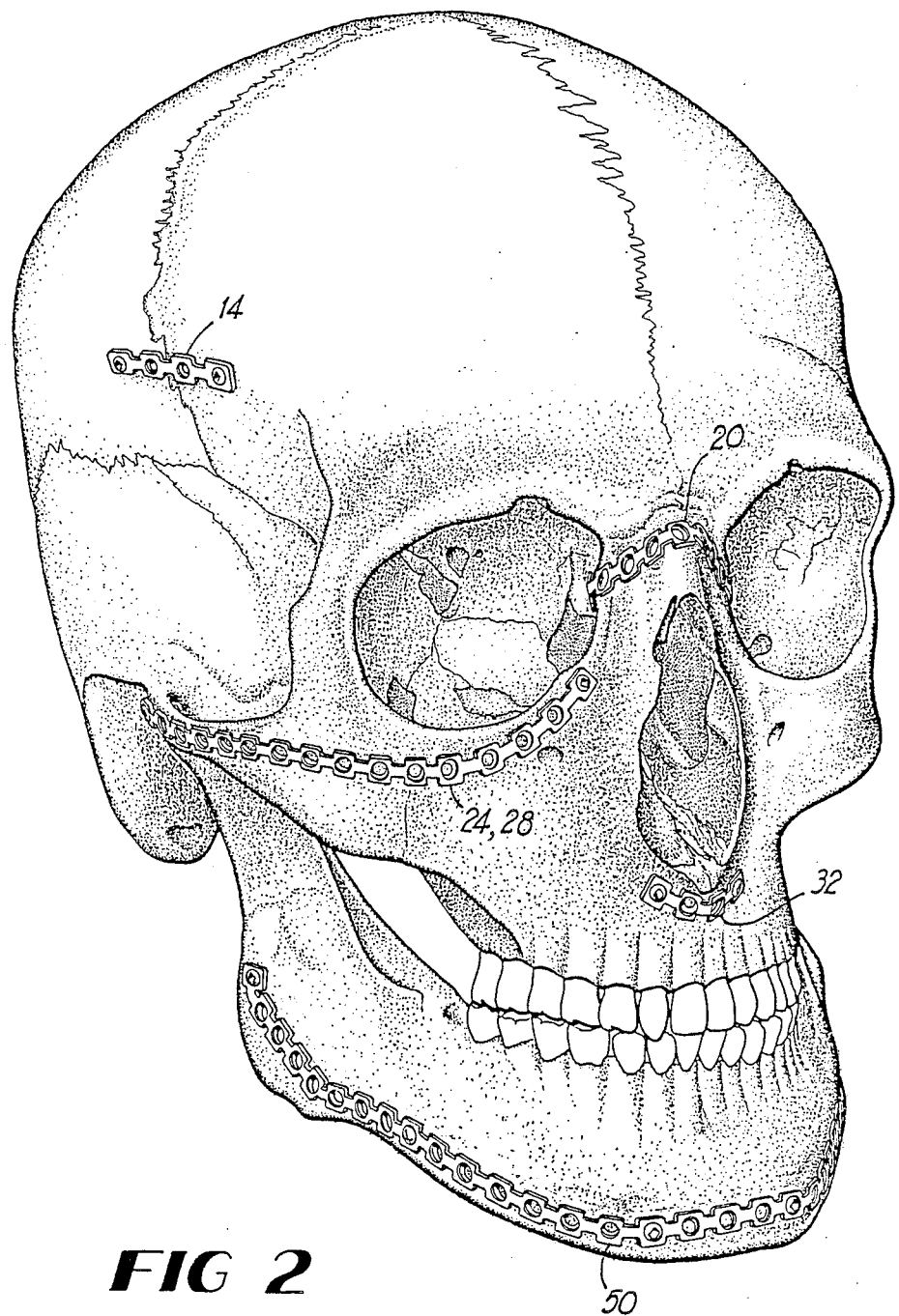
FIG. 2 is a perspective view of craniofacial structure showing additional installed bone stabilization plates according to the present invention.
Figure 3:
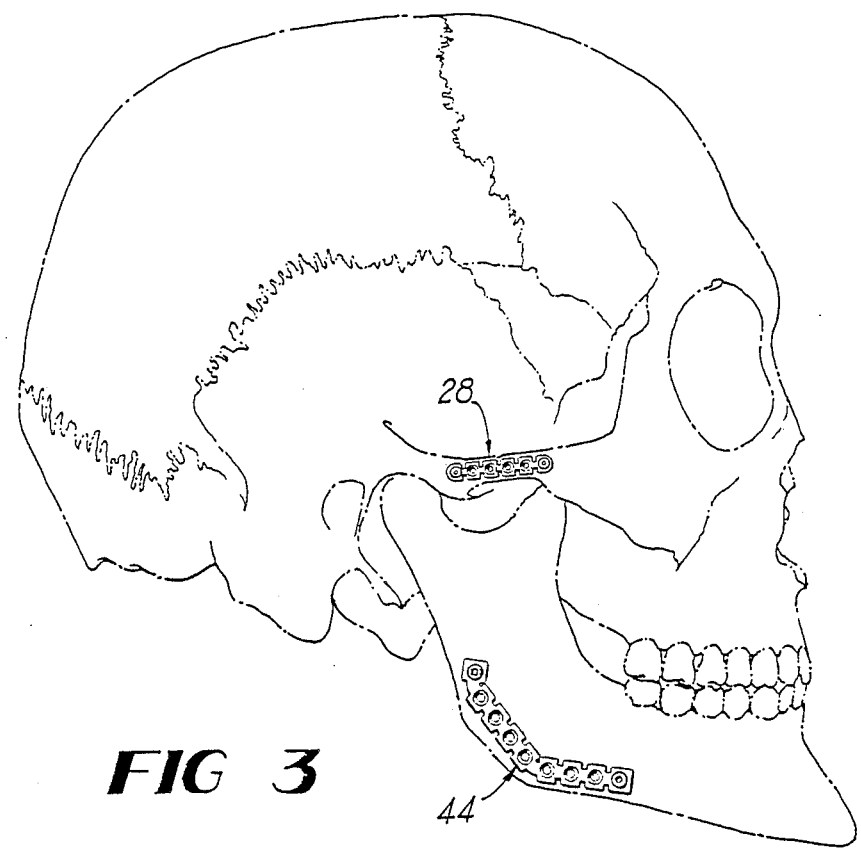
FIG. 3 is a side elevational view of craniofacial structure showing other installed bone stabilization plates according to the present invention.

FIGS. 1-3 illustrate configuration and placement of various osteosynthesis or bone stabilization plates 8 according to the present invention. The plates shown in these figures can be generally categorized as falling in the frontal or frontonasal, zygomatic, maxillary and mandibular groups.

The frontal group contains upper forehead plate 10, glabellar plate 12, panskull plate 14, nasofrontal suspension plate 16, utility plate 18 (not shown) and medial canthal reconstruction plate 20 shown in FIG. 2. The zygomatic group contains frontozygomatic suture plate 22, inferior orbital rim plate 24, lateral buttress plate 26 and zygomatic arch plate 28. The maxillary group contains medial buttress "T" 30, lateral buttress 26, inferior orbital rim (abbreviated) plate 24 (not shown); split palate plate 32, medial buttress "J" plate 34 and "L" plate 36. The mandibular group contains upper symphysis plate 38, marginal symphysis plate 40 (not shown), interior body plate 42, angle plate 44, ridge plate 46, posterior body plate 48 (not shown) and hemimandible plate 50 shown in FIG. 2. These plates are manufactured according to the present invention to be precontoured and secured to locations on the craniofacial skeleton corresponding with their names as generally shown in FIGS. 1-3.

Plates 8 according to the present invention, unlike earlier plates, are manufactured to correspond in three dimensions to their locations on the craniofacial skeleton. An example is lateral buttress plate 26 shown in FIGS. 1 and 13. Unlike earlier osteosynthesis plates, this plate is shaped during manufacture in the form of an "S" in its flat dimension. This dimension is referred to as the "face dimension 52." The plate is arched in the cross-sectional dimension perpendicular to the face dimension to form a convex top face 51 and a concave bottom face 53. This second dimension is referred to as the "cross-sectional dimension 54." Also unlike previous plates, the plate is shaped during manufacture in the third dimension to contour to the portion of the bone to which it will be attached. This third dimension, which is perpendicular to the face dimension 52 and the cross-sectional dimension 54, is referred to as the "contour dimension 56."

Figure 10:
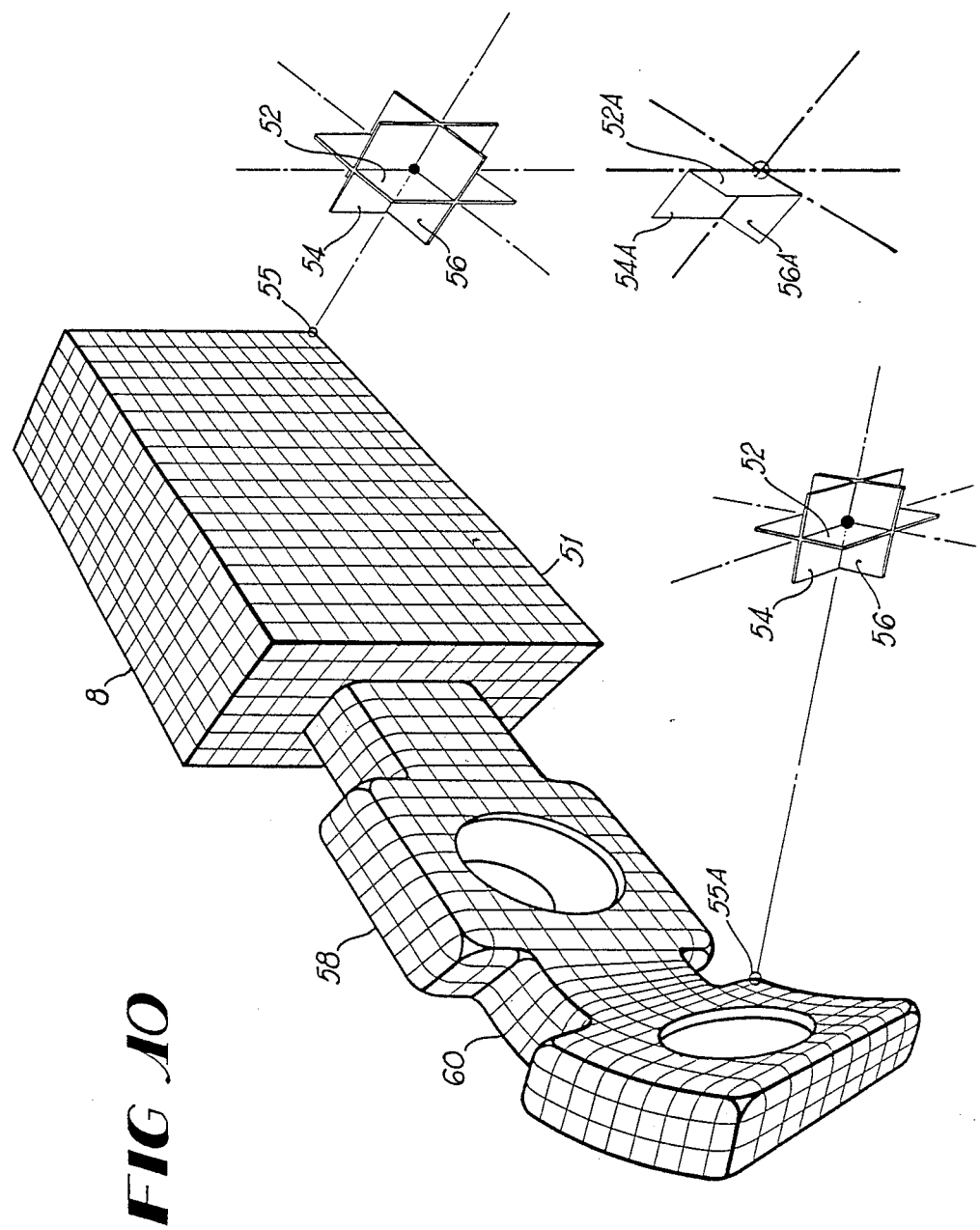
FIG. 10 is a perspective view of a plate according to the present invention showing absolute and relative reference systems used in connection with the plates.

Face dimension 52, cross-sectional dimension 54 and contour dimension 56 are illustrated in FIG. 10 which shows diagramatically a portion of a plate 8 according to the present invention formed from a hypothetical block of material. These dimensions correspond to the orientation of particular points on or within plate 8. Thus, face dimension 52 with respect to reference point 55 or 55A on top surface 51 of plate 8 is the plane which is tangent to top surface 51 at that point. Cross-sectional dimension 54 is the plane which contains point 55 or 55A, which is orthogonal to face dimension 52 and which contains the cross section of plate 8 at that point. Contour dimension 56 is the plane which is orthogonal to face dimension 52 and cross-sectional dimension 54 at reference point 55 or 55A.

If plate 8 were flat and straight, as are many conventional plates, then face dimension 52, cross-sectional dimension 54 and contour dimension 56 would correspond to face plane 52A, cross-sectional plane 54A and contour plane 56A as shown in FIG. 10. In such a case, face plane 52A would be tangent to all points on top surface 51, and all cross-sectional dimensions 54 of plate 8 would be orthogonal to top surface 51 and face plane 52A. Face dimension 52 and face plane 52A; cross-sectional dimension 54 and cross-sectional plane 54A and contour dimension 56 and contour plane 56A would therefore be coincident. Planes 52A, 54A and 56A thus define an absolute reference system while dimensions 52, 54, and 56 define a reference system that is relative with respect to locations on plates 8.

A plate 8 according to the present invention which is cast can have a crystalline structure which remains aligned even though the plate is contoured in three dimensions. By contrast, a conventional plate which must be bent and twisted significantly in the operating room requires deformation of the alignment of the plate's crystal lattices according to the angular differences in three dimensions between relative dimensions 52, 54 and 56 at any point in the plate and absolute planes 52A, 54A and 56A. Such deformation can cause weakness due simply to mechanical alterations in the crystalline structure and due to other effects such as frictional heat generated during bending and twisting. These can adversely affect hardness, stiffness and tensile strength. The present invention can thus minimize weaknesses in the structure of plates 8 which would otherwise be caused by excessive bending, twisting and contouring in the operating room.

Plates 8 can be made of stainless steel, titanium, vitallium (an alloy of cobalt, chromium and molybdenum) or other suitable, even non-metallic, materials. Stainless steel is subject to corrosion when exposed to electrolytes containing hydrogen and oxygen, so installed stainless steel plates may corrode over time and cause localized metallosis. Stainless steel is also subject to contact and friction, or fretting, corrosion. Stainless steel plates with protective coated highly polished surfaces can have better corrosion characteristics, but the surgical team must exercise great care not to damage this surface and affect corrosion potential.

Titanium is a softer metal then stainless steel and is frequently found not to be sufficiently rigid to withstand large forces placed on bone stabilization plates, particularly in the mandibular area. Vitallium is desireable because it can remain in the body for long periods of time without metallosis and need for removal, because it resists fretting, corrosion and oxidation, and because it is a particularly hard alloy.

Plates 8, because they are precontoured and require minimal bending and twisting in the operating room, are particularly well-suited to be made of polymeric, composite or other non-metallic materials which are not as easily shaped at room temperature as are metals. Plates 8 of such materials may also be manufactured to be resorbable in the body; such plates gradually wear away so that any irregularities transmitted through the patient's facial soft tissues diminish over time. Such resorbable materials include, for instance, compounds of polyglycolic acid.

Plates 8 are preferably cast, but they may be stamped, forged, cut, machined or formed by any other suitable or appropriate method. They may be shaped in the contour dimension 56 during casting, initial stamping or forging, or they may be shaped in a subsequent manufacturing step. After a plate 8 has been shaped or while it is being shaped as desired in all three dimensions, it may be subjected to a hardening or tempering process such as cycles of heating and quenching.

Figure 15:
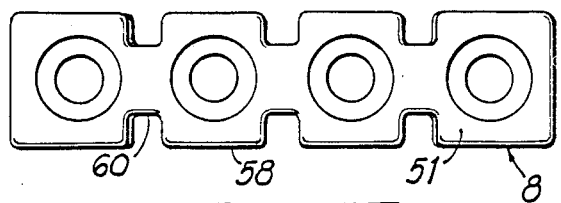
FIG. 15 is a face plane view of a plate of the present invention having a rectangular configuration for plate segments.
Figure 16:
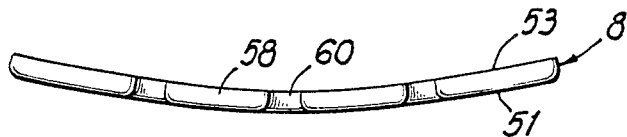
FIG. 16 is a contour plane elevational view of the plate of FIG. 15.
Figure 17:
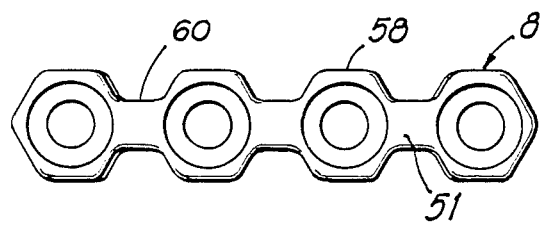
FIG. 17 is a face plane elevational view of a plate of the present invention having a second, hexagonal shaped segment configuration.
Figure 18:
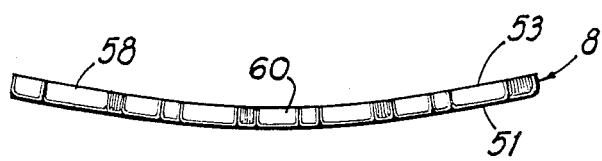
FIG. 18 is a contour plane elevational view of the plate of FIG. 17.
Figure 19:
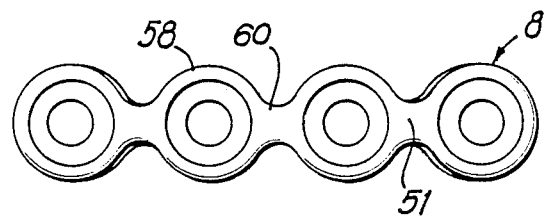
FIG. 19 is a face plane elevational view of a plate of the present invention with a third, generally circular shaped segment configuration.
Figure 20:
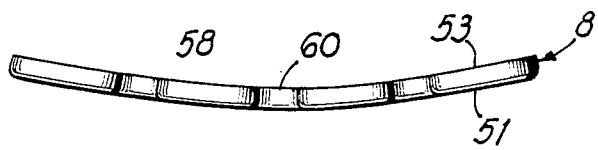
FIG. 20 is a contour plane elevational view of the plate of FIG. 19.

Plates 8 can, but need not, comprise a series of segments 58 connected by throat sections 60. Segments 58 may be generally rectangular as shown in FIGS. 15 and 16, generally hexagonal as shown in FIGS. 17 and 18, generally circular as shown in FIGS. 19 and 20 or of any other desired shape. Alternatively, plates 8 can exclude throat sections 60 so that their sides in the face dimension are continuous, as, for instance, linear, curvilinear or curved.

A plate 8 according to the present invention may be designed so that its cross-sectional moment of inertia or polar moment of inertia is constant. Such a plate has curved sides in its face dimension 52. Those curves, together with the screw hole definitions and the shape of the plate in the cross-sectional dimension, can be configured to provide a uniform polar moment of inertia in the cross-sectional dimension for uniform torsional resistance about the longitudinal axis, or a uniform moment of inertia in the cross-sectional dimension for uniform resistance to bending in the contour dimension. Plates 8 may also be constructed which satisfy both of these conditions for uniform twisting and bending in the contour dimension, and they may also have uniform moments of inertia in the contour or face dimensions for uniform resistance to bending or twisting or both. Such designs allow the plates to bend more predictably and thus be finally shaped in surgery more easily and quickly. Such moments of inertia may be calculated graphically, using incremental techniques or by any other appropriate method.

FIGS. 4, 5 and 6 illustrate a plate 8 according to the present invention with a uniform polar moment of inertia in the cross-sectional dimension 54. FIG. 6 schematically shows the concept of determining the polar moment of inertia, which is the integral of the product of each incremental area dA of the cross section multiplied by the square of its distance R from the center of gravity of the cross section. Because more area is located farther from the center of gravity in a cross section containing a screw hole S as shown, for example, in FIG. 5, the throat 60 cross sectional area as shown in FIG. 6 is larger than the segment 58 cross sectional area.

FIGS. 7, 8 and 9 demonstrate a plate design for uniform resistance to bending in the contour dimension. The moment of inertia about bending axis 66 as shown in FIGS. 8 and 9 is designed to be constant along longitudinal axis 62. This moment is defined as the integral of the product of incremental areas dA of the cross section multiplied by the square of their distance R from the axis 66.

FIGS. 11A and 11B show a front elevational and a plan view, respectively, of a glabellar plate 12 manufactured according to the present invention. The plate is configured in the face plane 52 to be generally U-shaped. It is also configured in the contour dimension 56 and the cross-sectional dimension 54 to conform to the skeleton. The contour dimension 56 configuration and the cross-sectional 54 dimension twist are also shown in FIG. 11B, the plan view of glabellar plate 12. FIGS. 11A and 11B demonstrate the subtlety and complexity of the curves required in the glabellar plate 12 to conform to the glabella.

FIGS. 12A and 12B show the more radically configured medial canthal plate 20, while FIG. 13 shows the nasofrontal separation plate 16. The lateral buttress plate 26, which is also radically configured, is shown in FIGS. 14A and 14B. These figures demonstrate the advantages to be gained by preconfiguring bone stabilization plates 8; curves in the plate are more continuous to reduce facial distortion in the patient, time is saved in the operating room, and the plates are subjected to far less metal fatigue and crimping because they need to be bent and twisted less in the operating room than previous plates. Plates 8 can also be made of harder and stiffer material because they require less bending in the operating room.

FIGS. 15-20 show various face plane configurations for segments 58 and throat sections 60 of plates 8.

FIGS. 22-27 show fasteners or screws 68 according to the present invention to secure plates 8 to the craniofacial skeleton. Screws 68 are preferably made of the same material as plates 8 to reduce electrolysis and galvanic erosion between plates 8 and screws 68 and consequent corrosion while plates 8 are in the patient. Screws 68 may be self-tapping as shown in FIGS. 22, 23, 25 and 26 or machine threaded as shown in FIGS. 24 and 27. Screws 68 may have convex or flat heads as shown in FIGS. 23-24 and 25-27 respectively. Significantly, screws 68 according to the present invention having heads with square recesses 72 have been shown to be advantageous in several respects. Square recess 72 minimizes inadvertent slippage or failure of the screwdriver-screw connection as screw 68 is torqued into the bone. Similarly, square recess 72 allows the screwdriver to remain aligned with the screw axis as torque is applied and thus helps to minimize misalignment of the screw in the skeleton.

Figure 21:
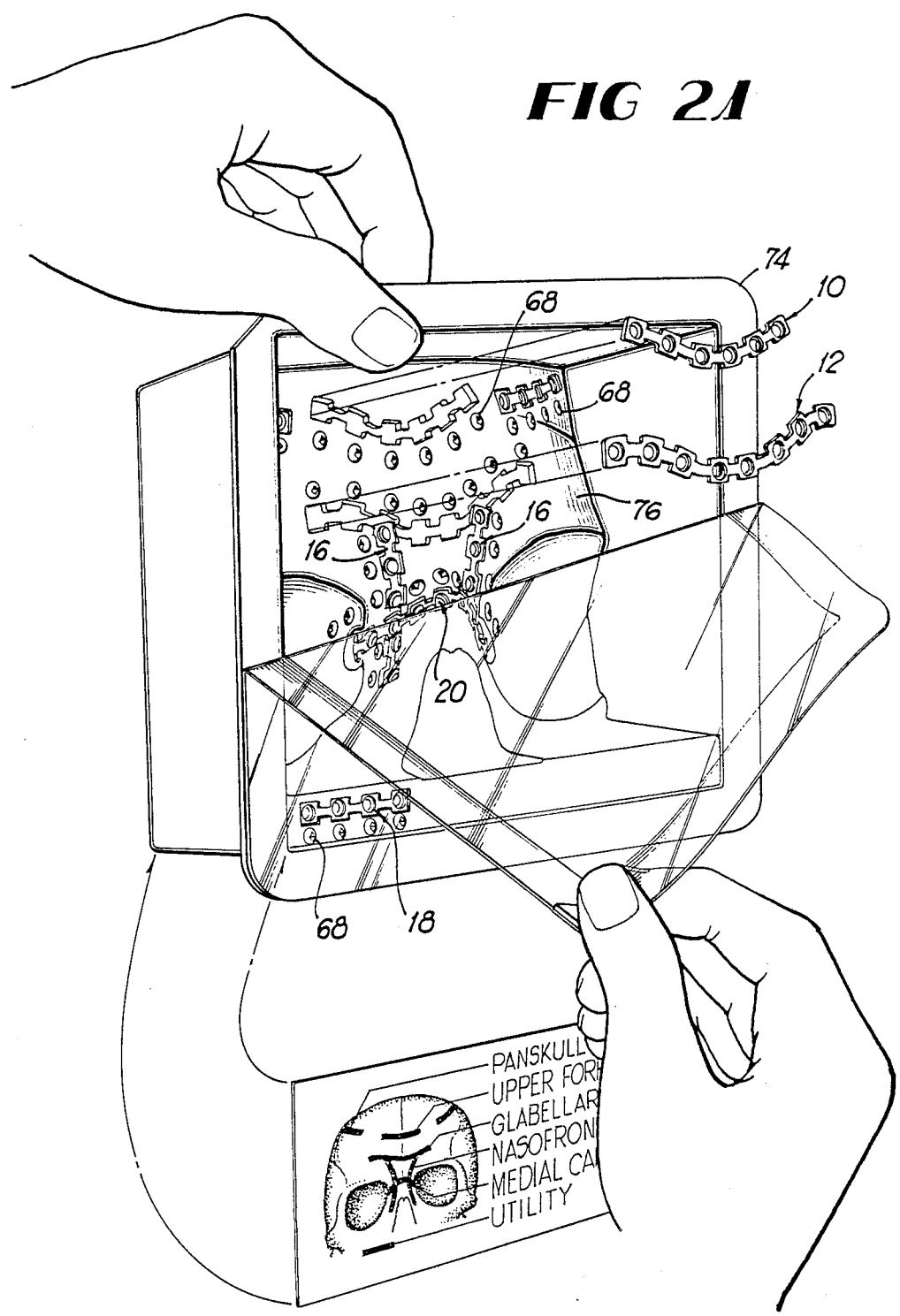
FIG. 21 is a perspective view of packaging for storing, transporting and presenting plates according to the present invention.

Plates 8 and screws 68 may be packaged as shown in FIG. 21 in a manner to allow all members of the surgical team easily to identify and refer to appropriate plates 8 and the screws 68 by which each plate 8 should be secured to the skeleton. They may also, of course, be packaged separately in individual packages. Packaging 74 contains a presentation face 76 to which plates 8 and screws 68 are secured. The packaging shown in FIG. 21 is for a frontal sinus separation case. It comprises upper forehead plate 10, glabellar plate 12, panskull plate 14, nasofrontal suspension plate 16, a utility plate 18 and a medial canthal plate 20. These are placed on the presentation face 76, which resembles a human face, at the locations corresponding to the skeletal sites to which they should be installed. Screws 68 can be inserted through holes in each plate 8 or inserted in presentation face 76 near their intended location in plates 8. Plates 8 which must be attached to thicker bones can thus be packaged on presentation face 76 with longer screws 68 while plates 8 which will be attached to thinner bone can be packaged with shorter screws 68. Additional screws 68 may be mounted on presentation face 76 near to screws they supplement. Plates 8 and screws 68 can be advantageously packaged in fourteen sets which correspond to fourteen groupings of craniofacial trauma and repair. These sets are presented in the following table:

I. Frontal Sinus Fracture
  A. Upper forehead 10
  B. Glabellar 12
  C. Two panskull 14
  D. Utility plate 18

II. Frontal Sinus with Nasofrontal Separation
  A. Upper forehead 10
  B. Glabellar 12
  C. Two panskull 14
  D. Nasofrontal suspension 16
  E. Utility 18
  F. Medial canthal "C" reconstruction 20

III. Zygomatic, right
  A. Frontozygomatic suture 22
  B. Inferior orbital rim 24
  C. Lateral buttress 26

IV. Zygomatic, Left
  A. Frontozygomatic suture 22
  B. Inferior orbital rim 24
  C. Lateral buttress 26

V. Zygomatic, Complex, Right
  A. Frontozygomatic suture 22
  B. Inferior orbital rim 24
  C. Lateral buttress 26
  D. Zygomatic arch 28

VI. Zygomatic, Complex, Left
  A. Frontozygomat
  B. Inferior orbital rim 24
  C. Lateral buttress 26
  D. Zygomatic arch 28

VII. Maxillary, Lefort I or II
  A. Right medial buttress "T" 30
  B. Left medial buttress "T" 30
  C. Right lateral buttress 26
  D. Left lateral buttress 26
  E. Right inferior orbital rim 24 (abbreviated)
  F Left inferior orbital rim 24 (abbreviated)

VIII. Maxillary with Split Palate
  A. Split palate 32
  B. Right medial buttress "T" 30
  C. Left medial buttress "T" 30
  D. Right lateral buttress 26
  E. Left lateral buttress 26
  F. Right inferior orbital rim 24 (abbreviated)
  G. Left inferior orbital rim 24 (abbreviated)

IX. Mandibular Symphysis/Body, Right
  A. Upper symphysis 38
  B. Marginal symphysis 40
  C. Anterior body 42

X. Mandibular Symphysis/Body, Left
  A. Upper symphysis 38
  B. Marginal symphysis 40
  C. Anterior body 42

XI. Mandibular Angle/Body, Right
  A. Angle 44
  B. Ridge 46
  C. Posterior body 48

XII. Mandibular Angle/Body, Left
  A. Angle 44
  B. Ridge 46
  C. Posterior body 48

XIII. Mandibular, Comminuted/Complex, Right
  A. Hemimandible 50, spanning ramus to contralateral parasymphyss XIV. Mandibular, Comminuted/Complex, Left
  A. Hemimandible 50, spanning ramus to contralateral parasymphysis These packages represent the "lowest common denominators" of plates needed for typical injuries to the craniofacial skeleton. Other plates may be developed and other sets may be used. Many cases will require more than one package of plates. An auto accident victim with complex injuries in the sinus, orbital rim and ramus areas, for instance, may require frontal sinus, zygomatic and mandibular angle/body packages.

The fourteen types of packages can be more easily accounted for than the many types of plates 8 they contain. Plates 8 according to the present invention can thus more easily be ordered, stocked, obtained by the surgeon and charged to the patient's account. The packages may be presterilized so that valuable anesthesia time is not lost while the surgeon is waiting for plates 8 or screws 68 to be sterilized. This may be accomplished, for instance, by sealed presterilized packaging 74 with peel-back top whose contents may be sterilized during manufacture. Presentation face 76 may be of any convenient material such as polymeric foam, vacuum-formed plastic material or other appropriate materials. Plates 8 may also, of course, be packaged in conventional peel-back top packages, metallic boxes or other containers individually or in other groups.

Screwdriver 78, shown in FIG. 28, has a square protrusion 80 for cooperating with square recesses 72 in screws 68. The protrusion 80 penetrates deeply enough into recesses 72 to assure that the screwdriver torque axis is aligned with the screw axis in order to minimize misalignment of screw 68 in bone. The square configuration of protrusion 80 also reduces the likelihood that protrusion 80 will slip in or strip recesses 72 and screws 68, or that they will cause screwhead 70 to fail, as can happen with flathead or cruciform head screws.

Screw starters 82 according to the present invention can take the form of, among other things, a disposable or permanent unit 84 as shown in FIG. 29 used to transport screws 68 to the surgical field and start them into the bone, or collars 100 shown in FIGS. 28 and 30 which are used to transport screws 68 to the surgical field and align them with the bone to be penetrated.

Unit 84 may by cylindrically shaped with a shank 88 connected to a handle 90 and a head 92. Head 92 has a cavity 94 which captures screwheads 70 by friction, interference or other desired means. In the preferred embodiment, cavity 94 captures screwheads 70 by means of a frictional collar 96 within cavity 94. Collar 96 is of slightly smaller inner circumference than screwheads 70. Cavity 94 also has a square protrusion 98 which matches the square protrusion 80 on screwdriver 78 and thus which cooperates with square recesses 72 on screw 68. In use, a screw 68 is inserted head-first into cavity 94 so that protrusion 98 fits within recess 72 of the screw 68. Screw 68 may then be transported to the surgical field in unit 84 and started into the bone.

Alternatively, collar 100 illustrated in FIG. 30 may be utilized. Collar 100 is a truncated cylinder with a countersink 102 to receive the countersunk portion of head 70 of screw 68. The shank of screw 68 penetrates through the face 104 of collar 100 opposite the countersink 102. A tab 106 is attached to collar 100 for gripping it. Collar 100 may contain a fault as shown in FIG. 30 so that it fails when screw 68 is driven a certain distance into the bone or upon application of a predetermined pressure. Collar 100 can be equipped with a radiographic marker 110 for safety purposes. Screws 68 may be provided in packaging 74 already inserted through collars 100 so that screws 68 may be easily transported and started.

Figure 31:
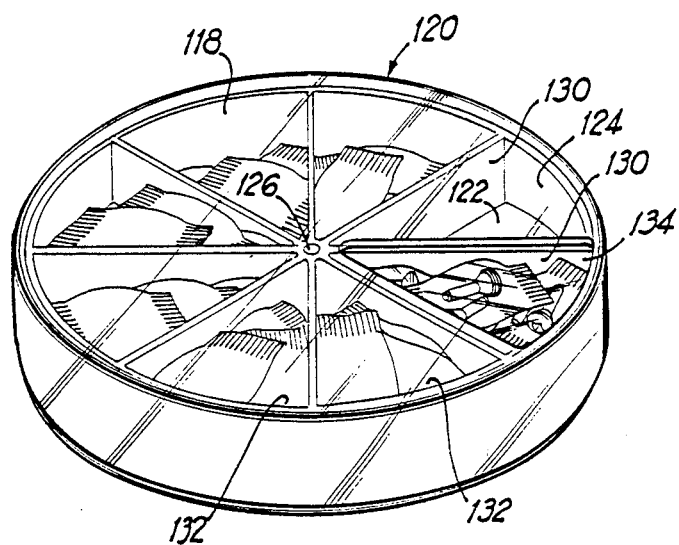
FIG. 31 shows a screw dispenser according to the present invention.

Screws 68 may also be dispensed from a dispenser 120. Dispenser 120 may take the form shown in FIG. 31 having a circular floor wall 122 connected to a cylindrical side wall 124. A pedestal 126 is connected to the center of the floor wall 122 and is rotatably attached to a circular cover 128. The dispenser 120 is divided into sections by a plurality of section walls 130 extending from the pedestal 126 to the side wall 124. Cover 128 has an opening 134 which corresponds in shape generally to a section 132. Cover 128 may thus be rotated to dispense various lengths of screws 68. Screws 68 may be packaged in presterilized plastic or other desirable packaging. Dispenser 120 may be mounted to an underlying surface with fasteners 136 such as screws or bolts. Similar dispensers 120 may be utilized for plates 8.

The parts, screws and instruments of the present invention allow for efficient and effective treatment. The surgeon evaluates the injury to determine which sets 74 of plates 8 are required. If the evaluation is inaccurate or incomplete, additional presterilized packages can be obtained immediately without the need to wait while additional plates are sterilized. The fracture is exposed and reduced. The surgeon determines which plates are to be applied, and the nurse easily understands which plates are needed because each plate 8 is situated in the packaging on presentation face 76 that resembles the portion of the skeleton on which the plate will be installed. Screws 68 packaged with the plates 8 are similarly easily identified.

The surgeon then performs any minor bending or crimping that may be required finally to tailor the contour of the plate to the skeleton to which it will be affixed. Screws 68 are then started using screwstarters 82 and finally driven using screwdriver 78. Screws 68 are then tightened to install the plate.

The foregoing is provided for illustration and description of the invention. Modifications and adaptations to the embodiments disclosed will be apparent to those of ordinary skill in the art and may be made without departing from the scope or spirit of the invention.

I claim:

1. Apparatus for osteosynthesis comprising:
   (a) at least one osteosynthesis plate shaped to conform in three dimensions to a portion of the facial skeleton, which plate has a changing radius of curvature from one point to the next along its longitudinal axis; and
   (b) a sealed container enclosing the osteosynthesis plate, which container includes a three dimensional model of said facial skeleton, said plate placed on the area of the facial skeleton model to which the plate is shaped to conform.

2. An apparatus as claimed in claim 1 in which the plate contains a top surface, an axis, and a first end, and is located in a reference system comprising:
   (a) a face plane tangent to the top surface of the plate at the first end; and
   (b) a contour plate orthogonal to the face plane and parallel to the axis at the first end of the plate.

3. An apparatus as claimed in claim 2 for stabilization of the palate in which:
   (a) the angle formed by the intersection of the top surface of the plate and the face plane of the plate is approximately 0° at the first end of the plate and decreases continuously to approximately −50° at the other end of the plate; and
   (b) the angle formed by the intersection of the axis of the plate and the contour plane of the plate is approximately 0°.

4. An apparatus as claimed in claim 2 for stabilization of the left inferior orbital rim in which:
   (a) the angle formed by the intersection of the top surface of the plate and the face plane of the plate is approximately 0° at the first end of the plate, increases continuously to approximately 60° at approximately 70% of the length of the axis from the first end, and then decreases continuously to approximately 0° at the other end; and
   (b) the angle formed by the intersection of the axis of the plate and the contour plane of the plate is approximately 0° at the first end of the plate and increases continuously to approximately 85° at the other end.

5. An apparatus as claimed in claim 2 for stabilization of the right inferior orbital rim in which:

(a) the angle formed by the intersection of the top surface of the plate and the face plane of the plate is approximately 0° at the first end of the plate, increases continuously to approximately 60° at approximately 70% of the length of the axis from the first end, and then decreases continuously to approximately 0° at the other end; and (b) the angle formed by the intersection of the axis of the plate and the contour plane of the plate is approximately 0° at the first end of the plate and decreases continuously to approximately −85° at the other end.

6. An apparatus as claimed in claim 2 for stabilization of the left medial buttress in which:
(a) the angle formed by the intersection of the top surface of the plate and the face plane of the plate is approximately 0° at the first end of the plate and decreases continuously to approximately −20° at the other end; and
(b) the angle formed by the intersection of the axis of the plate and the contour plane of the plate is approximately 0° at the first end of the plate and increases continuously to approximately 80° at the other end.

7. An apparatus as claimed in claim 2 for stabilization of the right medial buttress in which:
(a) the angle formed by the intersection of the top surface of the plate and the face plane of the plate is approximately 0° at the first end of the plate and decreases continuously to approximately −20° at the other end; and
(b) the angle formed by the intersection of the axis of the plate and the contour plane of the plate is approximately 0° at the first end of the plate and decreases continuously to approximately −80° at the other end.

8. An apparatus as claimed in claim 2 for stabilization of the left lateral buttress in which:
(a) the angle formed by the intersection of the top surface of the plate and the face plane of the plate is approximately 0° at the first end of the plate, decreases continuously to approximately −60° at approximately 80% of the length of the axis from the first end, and then increases continuously to approximately −15° at the other end; and
(b) the angle formed by the intersection of the axis of the plate and the contour plane of the plate is approximately 0° at the first end of the plate and increases continuously to approximately 45° at the other end.

9. An apparatus as claimed in claim 2 for stabilization of the right lateral buttress in which:
(a) the angle formed by the intersection of the top surface of the plate and the face plane of the plate is approximately 0° at the first end of the plate, decreases continuously to approximately −60° at approximately 80% of the length of the axis from the first end, and then increases continuously to approximately −15° at the other end; and
(b) the angle formed by the intersection of the axis of the plate and the contour plane of the plate is approximately 0° at the first end of the plate and decreases continuously to approximately −45° at the other end.

10. An apparatus as claimed in claim 2 for stabilization of the frontozygomatic suture in which:
(a) the angle formed by the intersection of the top surface of the plate and the face plane of the plate is approximately 0° at the first end of the plate and decreases continuously to approximately −20° at the other end; and
(b) the angle formed by the intersection of the axis of the plate and the contour plane of the plate is approximately 0°.

11. An apparatus as claimed in claim 2 for stabilization of the forehead in which:
(a) the angle formed by the intersection of the top surface of the plate and the face plane of the plate is approximately 0° at the first end of the plate and decreases continuously to approximately −20° at the other end; and
(b) the angle formed by the intersection of the axis of the plate and the contour plane of the plate is approximately 0° at the first end of the plate and decreases continuously to approximately −60° at the other end.

12. An apparatus as claimed in claim 2 for stabilization of the zygomatic arch in which:
(a) the angle formed by the intersection of the top surface of the plate and the face plane of the plate is approximately 0° at the first end of the plate, decreases continuously to approximately −30° at the approximately 80% of the length of the axis from the first end, and then increases continuously to approximately −15° at the other end; and
(b) the angle formed by the intersection of the axis of the plate and the contour plane of the plate is approximately 0°.

13. An apparatus as claimed in claim 2 for stabilization of the upper symphysis in which:
(a) the angle formed by the intersection of the top surface of the plate and the face plane of the plate is approximately 0°; and
(b) the angle formed by the intersection of the axis of the plate and the contour plane of the plate is approximately 0° at the first end of the plate and decreases continuously to approximately −70° at the other end.

14. An apparatus as claimed in claim 2 for stabilization of the marginal symphysis in which:
(a) the angle formed by the intersection of the top surface of the plate and the face plane of the plate is approximately 0° at the first end of the plate and decreases continuously to approximately −10° at the other end; and
(b) the angle formed by the intersection of the axis of the plate and the contour plane of the plate is approximately 0°.

15. An apparatus as claimed in claim 2 for stabilization of the left angle in which:
(a) the angle formed by the intersection of the top surface of the plate and the face plane of the plate is approximately 0°; and
(b) the angle formed by the intersection of the axis of the plate and the contour plane of the plate is approximately 0° at the first end of the plate, decreases to approximately −45° at approximately 13% of the length of the axis from the first end, and decreases to approximately −90° from approximately 65% of the length of the axis from the first end to the other end.

16. An apparatus as claimed in claim 2 for stabilization of the right angle in which:
(a) the angle formed by the intersection of the top surface of the plate and the face plane of the plate is approximately 0°; and (b) the angle formed by the intersection of the axis of the plate and the contour plane of the plate is approximately 0° at the first end of the plate, increases to approximately 45° at approximately 13% of the length of the axis from the first end, and increases to approximately 90° from approximately 65% of the length of the axis from the first end to the other end.

17. An apparatus as claimed in claim 2 for stabilization of the left ridge in which:
   (a) the angle formed by the intersection of the top surface of the plate and the face plane of the plate is approximately 0°; and
   (b) the angle formed by the intersection of the axis of the plate and the contour plane of the plate is approximately 0° at the first end of the plate, decreases to approximately −60° at approximately 30% of the length of the axis from the first end, and then increases to approximately 0° from approximately 70% of the length of the axis from the first end to the other end.

18. An apparatus as claimed in claim 2 for stabilization of the right ridge in which:
   (a) the angle formed by the intersection of the top surface of the plate and the face plane of the plate is approximately 0°; and
   (b) the angle formed by the intersection of the axis of the plate and the contour plane of the plate is approximately 0° at the first end of the plate, increases to approximately 60° at approximately 30% of the length of the axis from the first end, and then decreases to approximately 0° from approximately 70% of the length of the axis from the first end to the other end.

19. An apparatus as claimed in claim 2 in which the polar moment of inertia about the axis of the plate is substantially constant along the length of the axis.

20. An apparatus as claimed in claim 2 having a cover that is removably attached to the container walls.

21. An apparatus as claimed in claim 2 in which the plate is sterilized and the sealed container maintains the plate's sterility.

* * * * *